United States Patent [19]

Lywood

[11] Patent Number: 4,910,228
[45] Date of Patent: Mar. 20, 1990

[54] METHANOL

[75] Inventor: Warwick J. Lywood, Yarm, United Kingdom

[73] Assignee: Imperial Chemical Industries PLC, London, England

[21] Appl. No.: 307,907

[22] Filed: Feb. 9, 1989

[30] Foreign Application Priority Data

Feb. 18, 1988 [GB] United Kingdom ................ 8803766

[51] Int. Cl.$^4$ ...................... C07C 27/06; C07C 31/04
[52] U.S. Cl. .................................. 518/703; 518/704; 252/373
[58] Field of Search ................ 518/703, 704; 252/373

[56] References Cited

U.S. PATENT DOCUMENTS

| | | | |
|---|---|---|---|
| 3,763,205 | 10/1973 | Green | 518/704 |
| 4,479,925 | 10/1984 | Shires et al. | 252/373 |
| 4,695,442 | 9/1987 | Pinto | 423/359 |

Primary Examiner—Howard T. Mars
Attorney, Agent, or Firm—Cushman, Darby & Cushman

[57] ABSTRACT

A single pressure process for the production of methanol wherein the make-gas is produced by steam reforming a hydrocarbon feedstock, in admixture with recycled purge gas from the synthesis loop, at such a pressure that the make-gas can be fed without further compression, to the synthesis loop at a pressure no lower than the pressure at the inlet to said circulator. The reforming is effected by primary steam reforming followed by partial oxidation with oxygen and secondary reforming, without any bypass of the feedstock of the primary reforming stage, so as to give a make-gas of approximately stoichiometric composition for methanol synthesis. The primary reforming is effected at above 55 bar abs. over a catalyst disposed in tubes heated by passing the secondary reformed gas stream past the external surfaces of the reformer tubes in a direction counter-current to the flow of reactants undergoing primary reforming in said reformer tubes. In this way heat is transferred from said secondary reformed gas stream through the walls of said tubes to supply the endothermic heat of the steam reforming reaction.

In preferred forms of the process the steam is incorporated into the feed to the reformer by saturation and the excess of steam is removed from the reformed gas by direct contact with cold water: in this way a high pressure steam system recovering power from the reformed gas is not needed.

10 Claims, 0 Drawing Sheet

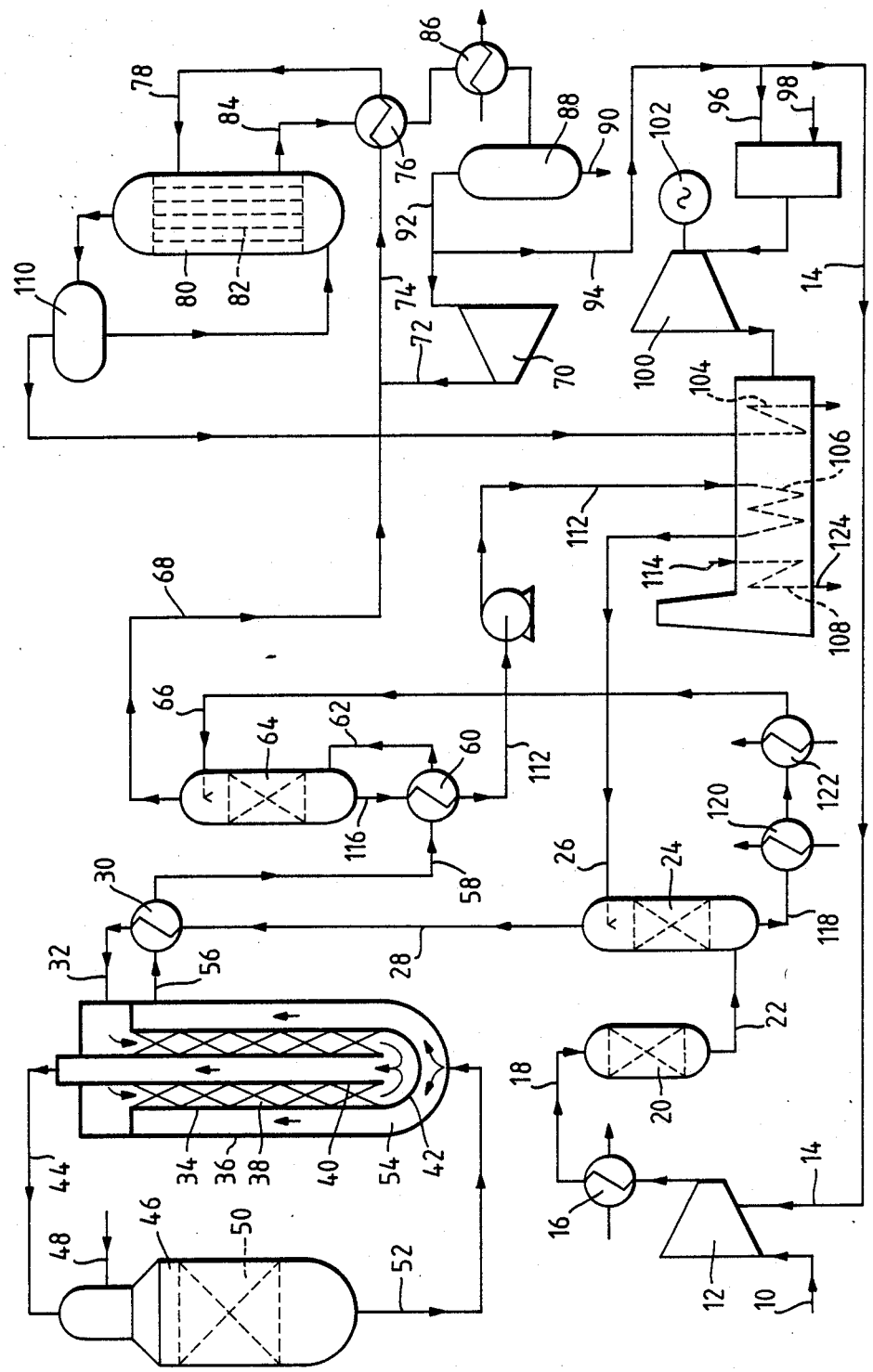

METHANOL

This invention relates to the production of methanol, and in particular to a low pressure (50–100 bars abs) process for the synthesis thereof.

Methanol is normally produced from a synthesis gas comprising hydrogen, carbon monoxide, and carbon dioxide in a synthesis loop comprising a synthesis reactor wherein synthesis gas is reacted to form methanol, a separator wherein methanol is separated from unreacted gas, and a circulator to effect recycle of unreacted gas to the synthesis reactor. Fresh synthesis gas, hereinafter referred to as make-gas, is fed to a suitable point in the loop, and a purge is taken from the loop to maintain the level of inert gases in the loop at a desired level. These inert gases are normally methane and nitrogen and result from the presence of such gases in the make-gas added to the loop.

The make-gas is conventionally produced by subjecting a mixture of steam and a hydrocarbon feedstock consisting predominantly of methane, eg natural gas, to primary steam reforming over a catalyst disposed in heated tubes, followed by cooling of the reformed gas to below the dew point of steam, and subsequent separation of the condensed water from the reformed gas stream. Conventionally the purge stream is used as part or all of the fuel required to heat said tubes, although there have been proposals, eg in Supp et al US-A-4271086 and Konoki et al US-A-4219492, to recycle loop purge to the reformer as part of the feed. In order to obtain efficient reforming and a low methane content in the make-gas, the reforming is conventionally effected at a pressure of the order of 10–30 bar abs. As such pressures are too low for efficient synthesis, the make-gas, after the separation of the unreacted steam, is compressed to the loop pressure. The compressor, commonly termed a make-gas compressor, required to effect this compression is normally powered by high pressure steam raised in heat exchanges effecting cooling of the reformed gas to below the steam dew point.

It is desirable to simplify the process of elimination of the make-gas compressor so that the make-gas is delivered to the loop at a pressure no less than the circulator inlet pressure. Such a process, hereinafter termed a single pressure process, has been proposed in the aforesaid Konoki et al reference. Konoki et al however envisaged that the reforming and synthesis pressures would be in the range 30-50 kg.cm$^{-2}$ gauge, ie approximately 30–50 bar abs. Because of the relatively low synthesis pressure, the equilibrium concentration of methanol in the reacted synthesis gas is relatively low. It would clearly be desirable to operate at higher pressures: however the use of higher reforming pressures not only presents serious metallurgical problems in conventional reforming operations but also gives rise to an increase in the methane content of the reformed gas, and hence in the make-gas.

Another problem associated with methanol synthesis wherein the make-gas is made by primary steam reforming a feedstock consisting predominantly of methane is that the resultant make-gas is hydrogen-rich: this inevitably leads to some inefficiency in the process even though the excess of hydrogen can be removed from the synthesis loop in the purge and used as fuel. Desirably the make-gas, and hence the synthesis gas, should be near stoichiometric for methanol synthesis: thus it should have a R value of about 2, where R is the ratio of the difference of the hydrogen and carbon dioxide molar contents to the total molar carbon oxides content. As disclosed in eg the aforesaid Supp et al reference, substitution of carbon dioxide from an external source for part of the steam employed for reforming, or, as disclosed in the aforesaid Konoki et al reference, addition of carbon dioxide from such a source to the reformed gas, are methods of at least partially correcting the stoichiometry. However such a source of carbon dioxide is not always available.

Another way of correcting the stoichiometry is by a combination of primary steam reforming and partial oxidation with oxygen, see for example Banquy GB-A-1569014, Ilgner et al GB-A-2099846, Herbort et al GB-A-2181740, Fiddler et al GB-A-2179366, and Marschner et al "Methanol Synthesis" Chapter 6 of "Applied Industrial Catalysis", Volume 2 at pages 229–230.

The aforesaid Herbort et al and Fiddler et al references disclose that the gas stream leaving the partial oxidation step can be used to supply the heat for the primary steam reforming stage. With that type of arrangement, the metallurgical problems associated with reforming at high pressures associated with conventional primary steam reforming, viz the problems associated with the combination of substantial pressure differences across the reformer tube walls and high temperatures, are alleviated and so higher reforming pressures can be adopted.

We have realised that, by the adoption of such an arrangement in a single pressure process, it is possible to devise a simplified, efficient, overall methanol process operating at higher pressures than envisaged by Konoki et al, despite the fact that the higher reforming pressure gives an increase in the methane content of the make-gas.

The aforesaid Banquy, Herbort et al, Fiddler et al, and Marschner et al, references indicate that part of the feedstock should bypass the steam reforming stage and be fed directly to the partial oxidation stage. Such a bypass presents difficulties in introducing the fresh feed to the partial oxidation stage: thus specially designed mixing/burner arrangements are required, for example as described by Herbort et al, to overcome the risk of thermal cracking, with consequent carbon deposition, of the hydrocarbons in the fresh feed fed to the partial oxidation stage. Furthermore we have found that such a bypass is in fact disadvantageous in the overall process.

Accordingly the present invention provides a single pressure process for the production of methanol in a synthesis loop having a synthesis reactor, a separator, and a circulator effecting circulation of gas around said loop, comprising
 (a) producing a make-up gas by:
   (i) forming a mixture of steam, a feedstock consisting predominantly of methane, and recycled purge gas removed from the loop;
   (ii) subjecting said mixture to primary steam reforming at a pressure above 55 bar abs. over a catalyst disposed in externally heated tubes;
   (iii) subjecting the primary reformed gas stream, without addition of any further feedstock, to partial oxidation by combustion with oxygen and passing the combustion products over a secondary steam reforming catalyst to bring the mixture towards equilibrium so as to give a secondary reformed gas stream containing unreacted steam, the amount of oxygen employed being such that the ratio R is in the range 1.8 to 2.2, where R is the ratio of the difference of the hydrogen and carbon dioxide molar contents to the total molar carbon oxides content; and said external heating of the reformer tubes being effected by passing the secondary reformed gas stream past the external surfaces of the reformer tubes in a direction counter-current to the flow of reactants undergoing primary reformin in said reformer tubes, whereby heat is transferred from said secondary reformed gas stream through the walls of said tubes to supply the endothermic heat of the primary steam reforming reaction; and (iv) cooling the secondary reformed gas stream to below the dew point of the steam therein to condense unreacted steam as water and separating said condensed water;

said reforming and separation of condensed water being effected at such pressure that the resulting make-up gas is produced at a pressure no lower than the pressure at the inlet to said circulator;

(b) adding said make-gas to said synthesis loop without further compression after reforming;

(c) passing a mixture of synthesis gas, including loop recycle gas, over a synthesis catalyst in said synthesis reactor at a pressure in the range 50–100 abs., thereby forming methanol and unreacted gas;

(d) separating synthesised methanol from unreacted gas in said separator;

(e) recycling unreacted gas from said separator as said loop recycle gas;

(f) removing gas from the loop as purge gas and using part of the purge gas as said recycled purge gas; and (g) discharging the remainder of the purge gas.

By the term reforming pressure we mean the pressure at the outlet of the reformer tubes. By the term synthesis pressure we mean the pressure at which the synthesis gas enters the synthesis catalyst. The reforming and synthesis pressures are preferably each effected at a pressure above 55 bar abs.

The loop circulator effects recompression of the loop recycle gas to the synthesis pressure: the loop recycle gas is normally at a pressure below the synthesis pressure as a result of pressure drops ocurring, for example, as the gas stream passed through the catalyst bed, or beds, in the synthesis reactor. However, these pressure drops are relatively small so that, at the inlet to the circulator, the loop recycle gas has a pressure of at least 85%, particularly at least 90%, of the synthesis pressure.

In one form of the invention the reforming stage is effected at such a pressure, that, after separation of the unreacted stream, the make-gas has a pressure substantially equal to the synthesis pressure: the make-gas can then be added to the loop recycle gas after the latter has left the circulator. In this form of the invention the omisson of a make-up gas compressor means that there is no need for a compressed make-up gas cooler. Thus the feedstock is compressed prior to the reforming stages to a pressure somewhat above the synthesis pressure to allow for pressure drops occurring in the stages of conversion of the feedstock to the make-gas.

In another form of the invention the degree of compression of the feedstock is such that the make-gas is supplied to the synthesis loop after the synthesis stage and prior to the inlet of the loop circulator at a pressure substantially equal to the pressure of the gas in the loop at the point of addition. In this way the circulator compresses the make-gas and the recycle gas to the synthesis pressure. In this case, if the make-gas is added to the loop between the methanol separator and the circulator inlet, to avoid condensation of water from the make-gas in the circulator, it may be necessary to cool the make-gas to a temperature that is at or below the temperature of the loop recycle gas, and to separate condensed water, prior to feeding the make-gas to the loop. However, if the make-gas is added to the loop between the synthesis reactor and the methanol separator, this cooling may be effected in the loop by the cooler used to cool the reacted synthesis gas to the methanol separation temperature.

In the process of the invention the feedstock may be methane or natural gas containing a substantial proportion, eg over 90% v/v methane. If the feedstock contains sulphur compounds, before, or preferably after, compression the feedstock is subjected to desulphurisation, eg hydrodesulphurisation and absorption of hydrogen sulphide using a suitable absorbent, eg a zinc oxide bed. Usually it is desirable to incorporate a hydrogen-containing gas into the feedstock prior to hydrodesulphurisation: as described hereinafter, part of the loop purge gas can be used as the hydrogen-containing gas.

Before, or preferably after, compression of the feedstock, steam is mixed with the feedstock: this steam introduction may be effected by direct injection of steam and/or by saturation of the feedstock by contact of the latter with a stream of heated water. The amount of steam introduced is preferably such as to give 1.4 to 3.0 moles of steam per gram atom of carbon in the feedstock. The amount of steam is preferably minimised as this leads to a more efficient process.

The resultant steam/feedstock mixture is then fed to a primary reformer. The reformer is of the type having a steam reforming catalyst, eg nickel on rings or pellets of a refractory support, disposed in tubes heated by a stream of secondary reformed gas flowing past the external surface of the tubes. A particularly suitable form of reformer is a "double-tube" reformer, ie a reformer where each reformer tube comprises an outer tube having a closed end and an inner tube disposed concentrically within the outer tube and communicating with the annular space between the inner and outer tubes at the closed end of the outer tube, with the steam reforming catalyst disposed in said annular space. One form of double-tube reformer is described in Pinto et al EP-A-124226. Another, particularly suitable, double tube reformer is described in Andrew et al EP-A-194067: in this reformer means, eg insulation, are provided to minimise the amount of heat transferred through the walls of the inner tube from the reformed gas that has left the catalyst containing zone and is passing out of the reformer through the inner tubes. The reformer is preferably operated so that the temperature of the reformed gas leaving the primary reforming catalyst is in the range of 600° to 800° C., particularly 650° to 750° C.

The primary reformed gas, optionally with additional steam, is then partially combusted with oxygen, typically obtained from a cryogenic air-separation plant, and the combustion products are then fed through a bed of a secondary steam reforming catalyst to bring the mixture towards equilibrium. The secondary reforming catalyst is preferably in the form of a precious metal, eg platinum, palladium, and/or rhodium supported on an alpha alumina honeycomb. An example of such a catalyst and secondary reforming process is described in Davidson et al EP-A-206535. The amount of oxygen employed is preferably such as to give a secondary reformed gas temperature at the outlet of the secondary reforming catalyst in the range 900° to 1100° C. The secondary reformed gas stream is then fed past the tubes of the primary reformer as the hot gas stream to supply the heat required for primary reforming. This transfer of heat from the secondary reformed gas to the primary reformer tubes results in partial cooling of the secondary reformed gas. The direction of flow of the secondary reformed gas is counter-current to the direction of flow of the steam/hydrocarbon feedstock mixture undergoing steam reforming in the tubes. In this way the temperature of the reactants undergoing reforming increases as those reactants pass along the tubes.

The use of this type of reforming wherein the secondary reformed gas is used to heat the primary reformer tubes has the advantage that the pressure differential across the primary reformer tubes is relatively small, being merely that resulting from the pressure drop the gas experiences as it passes through the primary reformer tubes and in the secondary reformer and associated pipework. This means that the primary reformer tubes can safely be operated at higher pressures than is customary in conventional primary reforming wherein a separately fired furnace is employed. The primary reformer tubes can thus be of relatively light gauge material.

The partially cooled secondary reformed gas typically has a temperature in the range 400° to 550° C. and is then cooled below the dew point of steam to condense the steam as water. The initial part of the cooling may conveniently be by heat exchange with the feedstock/steam mixture, thereby preheating the latter prior to feeding to the primary reformer tubes.

The heat required for the reforming thus is derived from the partial combustion of the secondary reformed gas. The degree of partial combustion also determines the composition of the secondary reformed gas. It is found that the amount of oxygen required to effect sufficient partial combustion is in approximate balance with that required to give a stoichiometric make-gas, if the primary reforming and secondary reforming stages, including any preheating of the feedstock/steam mixture with the partially cooled secondary reformed gas stream, are operated such that the temperature difference between the secondary reformed gas stream, after any such heat exchange with the feedstock/steam mixture, and the feedstock/steam mixture prior to any such preheating, is in the range of 120° to 290° C. The amount of oxygen employed is such that the aforesaid R ratio of the secondary reformed gas is in the range of 1.8 to 2.2, particularly in the range 1.9 to 2.1.

As mentioned hereinbefore, we have found that it is advantageous not to provide for part of the feedstock bypassing the reformer tubes. Thus, whereas the aforementioned Banquy, Fiddler et al, and Herbort et al, references suggest that 20% or more of the feedstock should bypass the reformer tubes, calculations show that with such a bypass, the heat exchange area, ie the area of the reformer tubes exposed to the secondary reformed gas, has to be significantly greater than where there is no such bypass. This means that, despite the smaller amount of reactants flowing through the tubes when there is such a bypass more, or longer, tubes have to be employed if there is a bypass of part of the feed. One reason for the use of a bypass is that it enables the steam to carbon ratio of the mixture in the tube to be increased, thereby decreasing the risk of carbon deposition in the tubes and on the catalyst therein, and yet the overall amount of steam maintained at the same level as if there were no bypass. However we have found that, because, as is explained hereinafter, the proportion of the loop purge that is recycled the reformer feed may be relatively high, the reactants mixture entering the reformer tubes contains a significant proportion of hydrogen: this decreases the risk of carbon deposition, even at relatively low steam ratios.

Further cooling of the secondary reformed gas after it has been used for heating the reformer tubes, and possibly for indirect heat exchange with the reactants to be fed to the reformer tubes, is conveniently by heat exchange with water. This may be indirect, producing steam and/or heated water, eg heated boiler feed water, or, particularly where steam is introduced into the feedstock by saturation, by direct heat exchange with a stream of cool water.

One feature of the invention is that the process may operated without the need for raising high pressure steam from the secondary reformed gas, and thus the plant can be simplified.

Thus in a conventional reforming process, heat is usually recovered from the hot reformed gas and from the flue gases from the furnace heating the reformer tubes, where a fired furnace is employed, by a steam power system wherein boiler feed water is heated, high pressure steam is raised and usually superheated, and then the high pressure steam is expanded in a turbine with the recovery of power, eg for export as electricity or for compression of the make-gas. Often it can be arranged that the exhaust from the turbine is at a suitable pressure for use as process steam, ie for use in the reforming process.

However, such a power steam system recovering heat from the reformed gas and from the furnace flue gas often produces more steam than is required, resulting in a considerable steam and/or power export. This is not always advantageous and so it would be often be desirable to eliminate the steam power system at least in so far as it is recovering heat from stages employed to produce the make-gas.

A system for the production of ammonia synthesis gas wherein a double tube reformer in which the tubes are heated by the secondary reformed gas and which does not employ a power steam system is disclosed in FIG. 4 of Pinto et al U.S. Pat. No. 4695442. A modification of that arrangement may be used in the present invention. Thus, in the present invention, as the secondary reformed gas is partially cooled by providing the heat required for reforming and possibly also by heat exchange with the reactants before they are fed to the reformer tubes, as in the aforesaid FIG. 4, a steam power system recovering heat from the make-gas formation stages may be eliminated. Thus the secondary reformed gas may be cooled by heat exchange with a stream of water in order to produce a stream of hot water which may then contacted with the feedstock to saturate the latter to form a feedstock/steam mixture suitable for use as the feed to the reformer tubes. After cooling the reformed gas, the unreacted steam is removed from the reformed gas by further cooling to below the dewpoint of the steam in the gas stream followed by separation of the condensed water. The separated condensed water may be used as part of the water stream that is heated by the aforesaid heat exchange. In some cases, and as shown in the aforesaid FIG. 4, it is possible to effect the cooling of the reformed gas to below the dew point, and the separation of condensed water, in a single stage by direct contact of the reformed gas, after use for the aforesaid reformer reactants preheating, with a stream of water, giving a stream of hot water which is then used for saturation of the feedstock.

In a preferred process therefore, the secondary reformed gas, after use for heating the reformer tubes, is cooled by heat exchange with the reactants to be fed to the reformer tubes, to give a partially cooled secondary reformed gas stream. The latter is then further cooled by indirect heat exchange with a stream of water, and then cooled to below the dew point by direct contact with a stream of cool water, giving a stream of hot water, containing the condensed stream, which is then used as the stream of water used for the aforesaid indirect heat exchange partially cooled secondary reformed gas. The stream of hot water from this indirect heat exchange is then used, preferably after further heating as described hereinafter, as the water stream employed to saturate the feed to the reformer tubes.

Such direct heat exchange with cool water as aforesaid will also effect sufficient removal of condensed water from the secondary reformed gas to give the make-gas. Where the cooling of the secondary reformed gas stream is by such direct heat exchange and the resultant hot water is used for saturation, the excess of water leaving the saturator may be used for other heating purposes, eg in a methanol distillation stage, giving a water stream which, possibly after further cooling, is used a the cool water stream for the direct heat exchange with the partially cooled secondary reformed gas.

After cooling the secondary reformed gas stream and separating the condensed water, eg in a catchpot if the cooling was not by direct heat exchange as aforesaid, the resultant make-gas is mixed with loop recycle gas at a suitable point in the synthesis loop and fed to the methanol synthesis stage. As mentioned above, in the present invention, only if the make-gas is added to the loop between the synthesis reactor and the circulator inlet is there any compression of the make-gas prior to feeding to the synthesis reactor, and this compression is that effected by the circulator.

The methanol synthesis, which is conducted at a pressure in the range 50-100 bar abs., may be effected using a conventional copper-based methanol synthesis catalyst. It may be effected in a synthesis reactor of the quench converter type or in a reactor in which the catalyst bed has immersed therein heat exchange tubes through which the synthesis gas passes en route to the catalyst bed, for example as described in Pinto EP-A-82070. Alternatively, and preferably, there may be used a reactor of the tube cooled type, for example as described in Pinto EP-A-81948, where the exothermic heat of methanol synthesis is removed by flow of a coolant, particularly water, through coolant tubes disposed in the catalyst bed, or beds. This type of reactor may be operated such that water as a coolant is converted into high pressure steam, ie steam at a pressure of above 30 bar abs., which is used for example as process steam, and/or to drive turbines thus recovering power. The recovered power may be used for producing the compressed oxygen from atmospheric pressure air, eg in a cryogenic plant, and/or for compressing the feedstock from the supply pressure, and/or for compressing the recycled loop purge if any recompression thereof is necessary, and/or for driving the loop circulator. As will be explained hereinafter, in preferred forms of the invention, power recovered from high pressure steam raised in such a converter may be used to supplement the power recovered from combustion of that part of the loop purge that is not recycled to the reformer feed. Alternatively, as described hereinafter, by the use of other types of converter, eg a quench converter, there need be no high pressure steam system.

After synthesis the reacted gas is cooled to condense methanol as an aqueous solution which is separated, eg in a catchpot. Part of the cooling is preferably by heat exchange with the synthesis gas to be fed to the converter in order to effect preheating of the latter to the desired synthesis inlet temperature, which is preferably in the range 200° to 280° C. Where there is no high pressure steam system, another part of the cooling of the reacted synthesis gas may be in a low pressure boiler producing steam at a pressure below 10 bar abs. Further cooling to effect condensation of the methanol may be with cooling air or water.

Part of the reacted synthesis gas from which methanol has been separated is recycled to the synthesis as the loop recycle gas. The remainder is purged from the loop in order to avoid a build-up of inerts, eg nitrogen (which is often present as an impurity in the natural gas and/or the oxygen), methane (resulting from incomplete reforming) and to avoid build-up of any excess of one or more reactants, eg resulting from the use of such an amount of oxygen that the ratio R of the make-gas is not equal to 2. Part of the purge is added to the feedstock prior to reforming: where the feedstock is subjected to hydrodesulphurisation prior to reforming, since the purge gas will contain hydrogen, it may be used as the hydrogen-containing gas required for hydrodesulphurisation as described above. Some recompression of the recycled purge is normally necessary. This recompression can be effected by adding the recycled purge gas to the feedstock prior to, or during, compression of the latter. However where the make-gas is supplied to the loop at a pressure below the synthesis pressure, eg by adding the make-gas to the loop at the circulator inlet pressure and the purge is taken at the synthesis pressure, eg from the circulator outlet, in some cases there will be no need for recompression of the recycled purge. This recycle of part of the purge of course does not remove inerts from the system. Accordingly part of the purge is not recycled but is discharged, to effect the desired removal of inerts such a nitrogen. This discharged purge may be used as fuel, preferably in a gas turbine recovering power indirectly as electricity and/or directly by using the gas turbine to drive the natural gas compressor and/or circulator. Heat may be recovered from the hot gas turbine effluent and used for superheating high pressurre steam, where there is a high pressure steam system, and/or for further heating hot water to be used for saturation of the feedstock, and/or for raising low pressure steam, and/or for preheating the feedstock prior to feeding to the saturator and/or reformer tubes.

It is preferred that the power recovered from any high pressure steam by means of steam turbines and power recovered from combustion of discharged loop purge in a gas turbine is sufficient to effect compression of the feedstock from the supply pressure to the reforming pressure, any necessary compression of the recycled loop purge to the reforming pressure, to power the circulator, and to produce the compressed oxygen from air at atmospheric pressure.

The amount of purge and the relative proportions thereof that are recycled to the reformer and discharged and combusted as aforesaid will depend on the power requirements of the process. Thus where there is a high pressure steam system, eg as a result of using a high pressure steam raising synthesis reactor, then power can be recovered from that high pressure steam: consequently less power need be recovered by combustion of discharged loop purge and so a smaller purge and/or a higher proportion thereof can be recycled to the reformer feed. However, the smaller the purge and/or the larger the proportion thereof that is recycled, the greater will be the inerts content of the loop. Since the methanol concentration in the reacted gas decreases as the inerts content increases, the optimum proportion of purge that is recycled will depend on the precise configuration of the flowsheet.

The separated aqueous methanol may be used as such or may be subjected to distillation. The heat required for distillation may be obtained from low pressure steam produced by letting down high pressure steam in a turbine or, where there is no high pressure steam system, from low pressure steam raised in cooling the reacted synthesis gas, and/or cooling of the secondary reformed gas stream. Alternatively, or additionally, heat required for distillation may be obtained from hot water streams produced in one or more of the stages of the production of the make-gas. For example heat for distillation may be obtained from the surplus hot water leaving a saturator used to saturate the feedstock.

One embodiment of the invention is illustrated by reference to the accompanying drawing which shows a flowsheet for the production of methanol from natural gas.

In the flowsheet natural gas of the following volume composition:

| | |
|---|---|
| methane | 92.2% |
| ethane | 3.1% |
| propane | 0.4% |
| butane | 0.1% |
| carbon dioxide | 0.5% |
| hydrogen | 1.5% |
| nitrogen | 2.2% | supplied at a pressure of 35 bar abs. is fed via line 10 to the first stage of a compressor 12. A purge recycle stream is added, via line 14, to the feedstock at an intermediate stage in the compressor. The resulting mixture, at a pressure of 83.5 bar abs., is then heated to 260° C. by heat exchange with steam in a heat exchanger 16 and fed, via line 18, to a vessel 20 containing a hydrodesulphurisation catalyst and a zinc oxide sulphur absorbent.

The resultant sulphur-free feedstock is then fed, via line 22, to a saturator 24 wherein it contacts a stream of hot water fed to the saturator via line 26. The saturated gas, consisting of a mixture of steam and feedstock, at a temperature of 251° C., is then fed, via line 28 to a heat exchanger 30 wherein it is preheated to 310° C.

The preheated gas is then fed, via line 32, to the outer tubes 34 of a double-tube reformer 36. The gas passes through a bed 38 of a nickel primary steam reforming catalyst in the annular space between the outer tube 34 and the inner tube 40 of each double reformer tube. At the lower end 42 of the tubes 34, the primary reformed gas has a temperature of about 750° C. The inner tubes 40 are insulated so that, as the gas passes up the inner tubes to the primary reformer exit, little heat is transferred from the primary reformed gas to the gas undergoing reforming in the primary reforming catalyst bed 38. The primary reformed gas leaves the primary reformer at about 710° C. and at a pressure of 80 bar abs. and is fed via line 44 to a burner in a secondary reformer 46. Oxygen ($O_2$ 99.5% $N_2$ 0.5%) preheated to 200° C. and at a pressure of 80.2 bar abs., is fed to the burner via line 48. Partial combustion of the primary reformed gas takes place and the resultant gas is fed through a secondary reformer catalyst 50 consisting of rhodium supported on an alpha alumina honeycomb. The amount of oxygen employed is such that the secondary reformed gas leaving the catalyst bed 50 via line 52 has an R ratio, as aforesaid, of about 2 and a temperature of about 1050° C.

The hot secondary reformed gas is then fed, via line 52, to the shell space 54 of the primary reformer where it is led past the outer tubes 34 to heat the latter, and leaves the primary reformer shell space via line 56 as a partially cooled secondary reformed gas at a temperature of 536° C. The partially cooled secondary reformed gas is then fed, via line 56, to heat exchanger 30 where it supplies the heat for preheating the feedstock/steam mixture and cools to about 488° C. The secondary reformed gas is then led, via line 58, to a further heat exchanger 60 wherein it heats a stream of water and then is fed, via line 62, to a desaturator 64 wherein the gas contacts a stream of cool water fed to the desaturator via line 66. The gas is thus cooled to below the dew point so that the steam in the secondary reformed gas condenses. The pressure drop in the hydrodesulphurisation, saturation, reforming, cooling, and desaturation stages is such that the water-depleted make-gas leaving desaturator 64 via line 68 has a pressure of 77.5 bar abs. This make-gas, typically at 80° C., is mixed with loop recycle gas, supplied from a loop circulator 70 at 77.5 bar abs. and 40° C. via line 72, to form the synthesis gas and is fed, via line 74, to a heat exchanger 76 wherein it is heated to the synthesis inlet temperature of 242° C.

The preheated synthesis gas is then fed at a pressure of 77.0 bar abs., via line 78, to a methanol synthesis converter 80 containing one or more beds of a copper based methanol synthesis catalyst in which tubes 82 carrying water under pressure as a coolant are immersed. The heat evolved during the methanol synthesis causes the water in the tubes to boil so that the converter is of the high pressure steam raising type. The reacted synthesis gas leaves the converter 80 via line 84 at 265° C. and passes through heat exchanger 76 and then through a second heat exchanger 86 where it gives up heat to cooling water. The reacted gas leaving heat exchanger 86 at 40° C. is fed to a catchpot 88 from which aqueous methanol is drawn off as bottoms via line 90 and fed to a distillation stage (not shown). The methanol-depleted reacted gas is fed, via line 92, to the circulator 70.

Prior to circulator 70 a purge stream is taken, via line 94, from the methanol-depleted gs. Part (about 58%) of the purge stream is recycled, via line 14, to the feedstock compressor 12, while the remainder of the purge is discharged, via line 96 and combusted with air fed via line 98. The combustion products drive a turbine 100 powering an alternator 102. Heat is recovered from the gas turbine exhaust by means of heat exchangers 104, 106, and 108 wherein, respectively, steam from a steam drum 110 supplied from tubes 82 is superheated, a water stream 112 is heated, and a make-up water stream 114 is preheated.

The heated water drawn off as bottoms from the desaturator 64 via line 116 is further heated in heat exchanger 60 and then forms the stream 112 heated in heat exchanger 106. The resultant hot water stream is used as the stream of hot water fed to saturator 24 via line 26. The excess of water added to saturator 24 is drawn off as bottoms via line 118, and is used to supply heat to the distillation stage via heat exchangers 120 and 122, before being returned to the desaturator via line 66 as the cool water stream. At a suitable point the preheated make-up water stream 124 from heat exchanger 108 is added to the saturator/desaturator circuit. The superheated steam produced from heat exchanger 104 may be let down in a turbine (not shown) with power recovery and the resultant low pressure steam used for heating the feedstock in heat exchanger 16 and/or to supply heat for the distillation of the methanol.

The calculated flow rates, pressures, and temperatures of the various gas streams for the production of approx 1530 te/day of methanol are shown in Table 1.

It is seen from Table 1 that the proportion of methane in the make-gas is relatively high (2.7%) as a result of the high reforming pressure, but as 58% of the loop purge is recycled, a large proportion of the methane in the make-gas is recovered and reused.

The power requirements for the Table 1 flowsheet, are very approximately as follows:

| | |
|---|---|
| To supply the oxygen at 80.2 bar abs: (Air compressor for the cryogenic oxygen plant and oxygen compressor delivering oxygen therefrom) | 14 MW |
| Natural gas and purge recycle compression: (Natural gas supplied at 35 bar abs.) | 2 MW |
| Circulator: | 2 MW |

About 60% of this power can be obtained from the gas turbine fuelled by the discharged portion 96 of the loop purge and the remaining power obtained from letting down steam raised at 40 bar abs in the synthesis converter to 3–4 bar abs. The resultant low pressure steam is sufficient to provide the needs of the methanol distillation.

As mentioned hereinbefore, advantages accrue from feeding all of the feedstock and steam to the reformer tubes rather than partially bypassing the reformer tubes. To illustrate this, in Table 2, there is shown the effect of a 20% bypass (ie 20% of the feed is fed directly to the partial oxidation zone by providing a bypass line, with an appropriate flow restriction valve, from line 22 to line 44). The same total amounts of feed, steam, and oxygen are employed, with the feed to the reformer tubes heated to the same temperature in the heat exchanger 30. In the bypass case, only the feed to the reformer tubes is saturated.

From Tables 1 and 2 it is seen that the primary reformer outlet temperature (stream 44) for the "bypass" case is somewhat greater than in the "no bypass" case. This means that the temperature difference across the outer walls of the reformer tubes is about 5% less in the "bypass" case that in the "no bypass" case, and so the heat exchange area required to effect this heat transfer is about 5% greater than in the "no bypass" case. Consequently a greater reformer tube surface area is required, eg more, or longer, tubes.

In Table 3 there is shown a flowsheet, also for the production of about 1530 te/day of methanol, using a reforming pressure of 60 bar abs. In this case the proportion of purge that is recycled is about 35%.

In the tables the streams are as follows:

| | |
|---|---|
| 10 feed | 68 make-gas |
| 14 recycle purge | 72 loop recycle |
| 28 saturated gas | 78 inlet to converter |
| 32 is the preheated reformer feed | 84 outlet from converter |
| 44 primary reformed gas | 90 product ex-catchpot |
| 48 oxygen | 92 gas ex-catchpot |
| 52 secondary reformed gas | 94 discharged purge |
| 56 secondary reformed gas leaving 36 | 96 fuel |
| 58 secondary reformed gas leaving 30 | |

TABLE 1

| Stream | Pressure (bar abs) | Temp (°C.) | Flow rate (kg mol. h$^{-1}$) | | | | | | | |
|---|---|---|---|---|---|---|---|---|---|---|
| | | | $CH_4$ | $CO_2$ | CO | $H_2$ | $N_2$ | $O_2$ | $H_2O$ | $CH_3OH$ |
| 10 | 35.0 | 20 | 2200.8* | 12.1 | — | 31.9 | 47.7 | — | — | — |
| 14 | 74.5 | 40 | 103.4 | 46.9 | 30.2 | 276.1 | 66.2 | — | 0.3 | 3.5 |
| 28 | 83.5 | 251 | 2304.2* | 59.0 | 30.2 | 303.5 | 113.9 | — | 3456.4 | 3.5 |
| 32 | 83.0 | 310 | 2304.2* | 59.0 | 30.2 | 303.5 | 113.9 | — | 3456.4 | 3.5 |
| 44 | 80.0 | 710 | 1916.0 | 326.5 | 154.5 | 1650.2 | 113.9 | — | 2800.6 | — |
| 48 | 80.2 | 200 | — | — | — | — | 5.4 | 1070.2 | — | — |
| 52 | 79.2 | 1050 | 202.4 | 533.4 | 1661.1 | 4857.4 | 119.3 | — | 3020.5 | — |
| 56 | 78.7 | 536 | 202.4 | 533.4 | 1661.1 | 4857.4 | 119.3 | — | 3020.5 | — |
| 58 | 78.2 | 488 | 202.4 | 533.4 | 1661.1 | 4857.4 | 119.3 | — | 3020.5 | — |
| 68 | 77.5 | 80 | 202.4 | 532.0 | 1661.1 | 4855.9 | 119.3 | — | 58.9 | — |
| 72 | 74.5 | 40 | 6117.7 | 2774.1 | 1789.1 | 16068.1 | 3916.0 | — | 16.1 | 205.5 |
| 78 | 77.0 | 242 | 6320.1 | 3306.1 | 3450.2 | 20924.0 | 4035.3 | — | 75.0 | 205.5 |
| 84 | 75.5 | 265 | 6320.1 | 2915.8 | 1844.5 | 16541.7 | 4035.3 | — | 465.3 | 2201.5 |
| 90 | 74.5 | 40 | 24.1 | 60.9 | 3.3 | 5.5 | 5.2 | — | 448.7 | 1990.0 |
| 92 | 74.5 | 40 | 6296.0 | 2854.9 | 1841.2 | 16536.2 | 4030.1 | — | 16.6 | 211.5 |
| 94 | 74.5 | 40 | 178.3 | 80.8 | 52.1 | 468.2 | 114.1 | — | 0.5 | 6.0 |
| 96 | 74.5 | 40 | 74.9 | 33.9 | 21.9 | 196.6 | 47.9 | — | 0.2 | 2.5 |

*Includes 172.5 kg mol. h$^{-1}$ of higher hydrocarbons expressed as $CH_{2.93}$

TABLE 2

| Stream | Pressure (bar abs) | Temp (°C.) | Flow rate (kg mol. h$^{-1}$) | | | | | | | |
|---|---|---|---|---|---|---|---|---|---|---|
| | | | $CH_4$ | $CO_2$ | CO | $H_2$ | $N_2$ | $O_2$ | $H_2O$ | $CH_3OH$ |
| 22 | 83.5 | 260 | 2304.2* | 59.0 | 30.2 | 303.5 | 113.9 | — | 0.3 | 3.5 |
| 28 | 83.5 | 258 | 1843.3+ | 47.3 | 24.2 | 242.8 | 91.2 | — | 3456.0 | 2.8 |

TABLE 2-continued

| Stream | Pressure (bar abs) | Temp (°C.) | CH4 | CO2 | CO | H2 | N2 | O2 | H2O | CH3OH |
|---|---|---|---|---|---|---|---|---|---|---|
| 32 | 83.5 | 310 | 1843.3+ | 47.3 | 24.2 | 242.8 | 91.2 | — | 3456.0 | 2.8 |
| 44 | 80.0 | 733 | 1427.9 | 318.5 | 171.1 | 1691.7 | 91.2 | — | 2769.5 | — |
| bypass | 80.2 | 260 | 460.9++ | 11.7 | 6.0 | 60.7 | 22.7 | — | 0.1 | 0.7 |
| 48 | 80.2 | 200 | — | — | — | — | 5.4 | 1069.9 | — | — |
| 52 | 79.2 | 1050 | 202.7 | 533.5 | 1660.8 | 4856.7 | 119.3 | — | 3020.2 | — |
| 56 | 78.7 | 532 | 202.7 | 533.5 | 1660.8 | 4856.7 | 119.3 | — | 3020.2 | — |
| 58 | 78.2 | 495 | 202.7 | 533.5 | 1660.8 | 4856.7 | 119.3 | — | 3020.2 | — |

*Includes 172.5 kg mol. h$^{-1}$ of higher hydrocarbons (CH$_{2.93}$)
+Includes 138.3 kg mol. h$^{-1}$ of higher hydrocarbons (CH$_{2.93}$)
++Includes 34.2 kg mol. h$^{-1}$ of higher hydrocarbons (CH$_{2.93}$)

TABLE 3

| Stream | Pressure (bar abs) | Temp (°C.) | CH4 | CO2 | CO | H2 | N2 | O2 | H2O | CH3OH |
|---|---|---|---|---|---|---|---|---|---|---|
| 10 | 35.0 | 20 | 2159.8* | 11.9 | — | 31.3 | 46.8 | — | — | — |
| 14 | 54.5 | 40 | 37.0 | 14.4 | 13.5 | 110.4 | 25.1 | — | 0.1 | 1.6 |
| 28 | 63.5 | 240 | 2196.8* | 26.3 | 13.5 | 141.7 | 71.9 | — | 3295.2 | 1.6 |
| 32 | 63.0 | 310 | 2196.8* | 26.3 | 13.5 | 141.7 | 71.9 | — | 3295.2 | 1.6 |
| 44 | 60.0 | 710 | 1738.5 | 323.2 | 176.4 | 1725.7 | 71.9 | — | 2540.0 | — |
| 48 | 60.2 | 200 | — | — | — | — | 5.1 | 1011.3 | — | — |
| 52 | 59.2 | 1050 | 124.6 | 491.5 | 1622.1 | 4723.4 | 77.0 | — | 2770.3 | — |
| 56 | 58.7 | 484 | 124.6 | 491.5 | 1622.1 | 4723.4 | 77.0 | — | 2770.3 | — |
| 58 | 58.2 | 429 | 124.6 | 491.5 | 1622.1 | 4723.4 | 77.0 | — | 2770.3 | — |
| 68 | 57.5 | 80 | 124.6 | 490.5 | 1622.1 | 4722.3 | 77.0 | — | 70.8 | — |
| 72 | 54.5 | 40 | 9288.2 | 3623.6 | 3388.5 | 27742.4 | 6302.0 | — | 32.2 | 391.4 |
| 78 | 57.0 | 242 | 9412.8 | 4114.1 | 5010.6 | 32464.7 | 6379.0 | — | 103.0 | 391.4 |
| 84 | 55.5 | 265 | 9412.8 | 3702.8 | 3430.7 | 28070.1 | 6379.0 | — | 514.6 | 2382.9 |
| 90 | 54.5 | 40 | 16.2 | 36.6 | 2.7 | 3.9 | 3.6 | — | 482.0 | 1987.0 |
| 92 | 54.5 | 40 | 9396.6 | 3665.9 | 3428.0 | 28066.2 | 6375.4 | — | 32.6 | 395.9 |
| 94 | 54.5 | 40 | 108.3 | 42.3 | 39.5 | 323.5 | 73.5 | — | 0.4 | 4.6 |
| 96 | 54.5 | 40 | 71.3 | 27.8 | 26.0 | 213.1 | 48.4 | — | 0.2 | 3.0 |

*Includes 169.3 kg mol. h$^{-1}$ of higher hydrocarbons expressed as CH$_{2.93}$

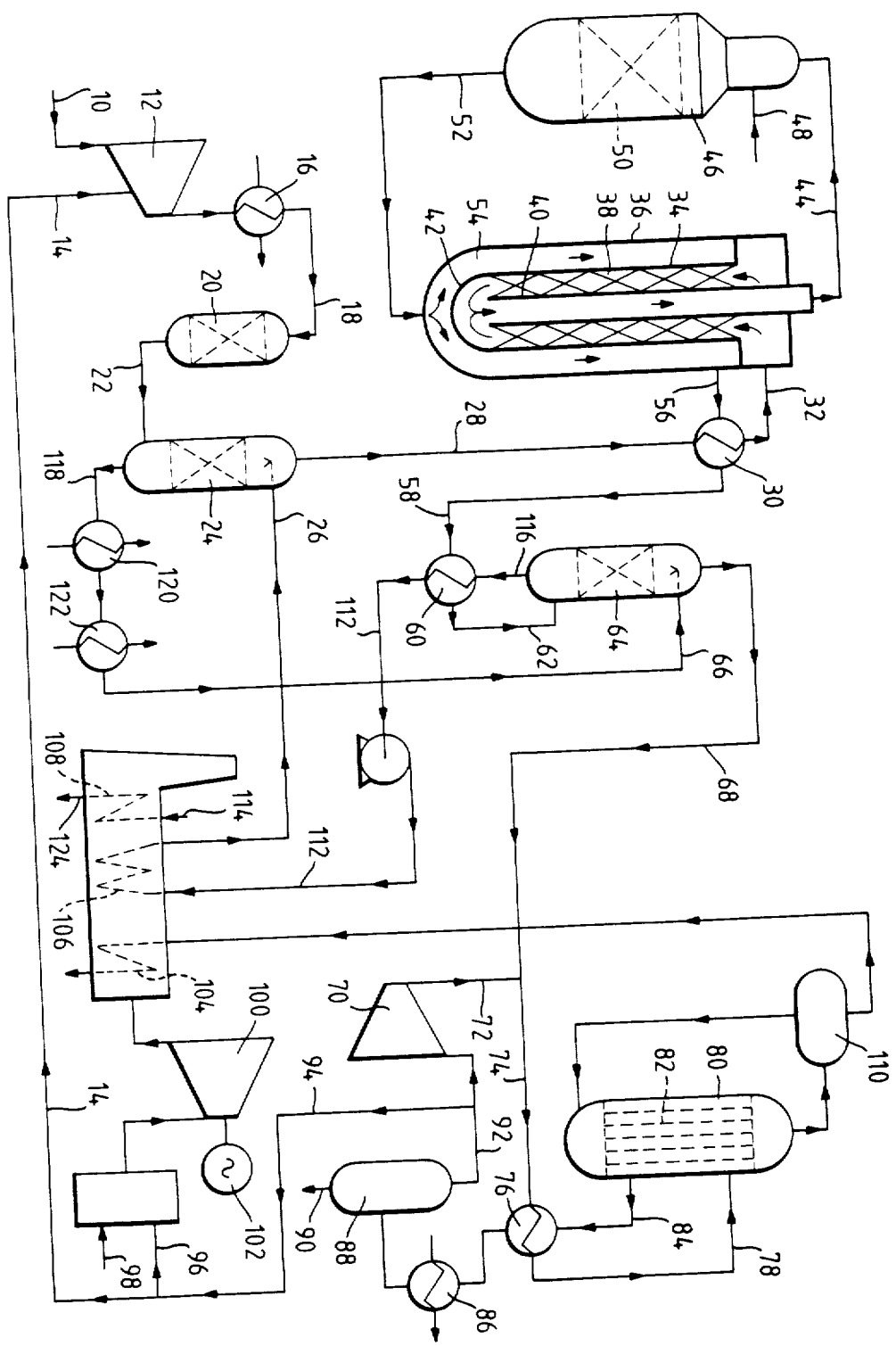

I claim:

1. A single pressure process for the production of methanol in a synthesis loop having synthesis reactor, a separator, and a circulator effecting circulation of gas around said loop, comprising
 (a) producing a make-up gas by:
   (i) forming a mixture of steam, a feedstock consisting predominantly of methane, and recycled purge gas removed from the loop;
   (ii) subjecting said mixture to primary steam reforming at a pressure above 55 bar abs. over a catalyst disposed in externally heated tubes;
   (iii) subjecting the primary reformed gas stream, without addition of any further feedstock, to partial oxidation by combustion with oxygen and passing the combustion products over a secondary steam reforming catalyst to bring the mixture towards equilibrium so as to give a secondary reformed gas stream containing unreacted steam, the amount of oxygen employed being such that the ratio R is in the range 1.8 to 2.2, where R is the ratio of the difference of the hydrogen and carbon dioxide molar contents to the total molar carbon oxides content; and
   said external heating of the reformer tubes being effected by passing the secondary reformed gas stream past the external surfaces of the reformer tubes in a direction counter-current to the flow of reactants undergoing primary reforming in said reformer tubes, whereby heat is transferred from said secondary reformed gas stream through the walls of said tubes to supply the endothermic heat of the primary steam reforming reaction; and
   (iv) cooling the secondary reformed gas stream to below the dew point of the steam therein to condense unreacted steam as water and separating said condensed water;
   said reforming and separation of condensed water being effected at such pressure that the resulting make-gas is produced at a pressure no lower than the pressure at the inlet to said circulator;
 (b) adding said make-gas to said synthesis loop without further compression after reforming;
 (c) passing a mixture of synthesis gas, including loop recycle gas, over a synthesis catalyst in said synthesis reactor at a pressure in the range 50–100 bar abs., thereby forming methanol and unreacted gas;
 (d) separating synthesized methanol from unreacted gas in said separator;
 (e) recycling unreacted gas from said separator as said loop recycle gas;
 (f) removing gas from the loop as purge gas and using part of the purge gas as said recycled purge gas; and
 (g) discharging the remainder of the purge gas.

2. A process according to claim 1 wherein the primary reforming is effected in a reformer where each reformer tube comprises an outer tube having a closed end and an inner tube disposed concentrically within the outer tube and communicating with the annular space between the inner and outer tubes at the closed end of the outer tube, with the steam reforming catalyst disposed in said annular space.

3. A process according to claim 1 wherein the reforming is effected at such a pressure, that, after the separation of condensed water, the make-gas has a pressure substantially equal to the synthesis pressure, and the make-gas is added to the loop between the circulator and the synthesis reactor.

4. A process according to claim 1 wherein the secondary reformed gas, after it has been used to heat the reformer tubes, is partially cooled by heat exchange with the steam/feedstock mixture to be fed to the reformer tubes.

5. A process according to claim 1 wherein the steam is incorporated into a mixture of the recycled purge gas and the feedstock by saturation by contact of that mixture with a stream of hot water.

6. A process according to claim 5 wherein the cooling of the secondary reformed gas, after the latter has been used to heat the reformer tubes, includes indirect heat exchange with a stream of water which is then used as the stream of hot water employed for the saturation of the mixture of the feedstock and recycled purge gas.

7. A process according to claim 5 wherein the cooling of the secondary reformed gas to below the dew point of the steam therein and the separation of the condensed water includes contact of the secondary reformed gas stream with a stream of water, thereby giving a stream of water including the condensed water, and that stream of water including the condensed water is heated and used as the stream of hot water employed for the saturation of the mixture of the feedstock and recycled purge gas.

8. A process according to claim 1 wherein power is recovered from the discharged portion of the purge gas by combustion thereof in a gas turbine.

9. A process according to claim 8 wherein the methanol synthesis is effected in heat exchange with boiling water under pressure, thereby raising high pressure steam, power is recovered from the resultant high pressure steam by expansion thereof to give low pressure steam in a steam turbine, and the proportion of purge gas that is discharged and combusted is such that the power recovered from the turbines is sufficient to effect compression of the feedstock from the supply pressure to the reforming pressure, any necessary compression of the recycled purge gas to the reforming pressure, to power the circulator, and to produce the compressed oxygen from air at atmospheric pressure.

10. A process according to claim 8 wherein heat is recovered from the reacted methanol synthesis gas by indirect heat exchange with water producing low pressure steam and there is no generation of high pressure steam and power recovery therefrom, and the proportion of purge gas that is discharged and combusted is such that the power recovered therefrom is sufficient to effect compression of the feedstock from the supply pressure to the reforming pressure, any necessary compression of the recycled purge gas to the reforming pressure, to power the circulator, and to produce the compressed oxygen from air at atmospheric pressure.

* * * * *

UNITED STATES PATENT AND TRADEMARK OFFICE
CERTIFICATE OF CORRECTION

PATENT NO. : 4,910,228

DATED : March 20, 1990

INVENTOR(S) : Lynwood

It is certified that error appears in the above-indentified patent and that said Letters Patent is hereby corrected as shown below:

The Drawing sheet should be added as shown on the attached page.

Signed and Sealed this

Twenty-first Day of September, 1993

Attest:

BRUCE LEHMAN

*Attesting Officer*  *Commissioner of Patents and Trademarks*